United States Patent [19]
Giles

[11] Patent Number: 6,090,065
[45] Date of Patent: Jul. 18, 2000

[54] SELF-CYCLING BREAST PUMP

[75] Inventor: John P. Giles, Atlanta, Ga.

[73] Assignee: Evenflo Company, Inc., Vandalia, Ohio

[21] Appl. No.: 09/110,222

[22] Filed: Jul. 6, 1998

[51] Int. Cl.[7] .................................................. A61M 1/06
[52] U.S. Cl. .............................. 604/74; 604/315; 604/346
[58] Field of Search ................................ 604/73, 74, 310, 604/313, 315, 316, 312; 417/435, 440

[56] References Cited

U.S. PATENT DOCUMENTS

| | | |
|---|---|---|
| 1,847,658 | 3/1932 | Lasker . |
| 2,162,076 | 6/1939 | Frimand ................................ 128/128 |
| 4,111,204 | 9/1978 | Hessel .................................. 128/276 |
| 4,311,141 | 1/1982 | Diamond .............................. 128/281 |
| 4,583,970 | 4/1986 | Kirchner ................................. 604/74 |
| 4,673,388 | 6/1987 | Schlensog et al. .................... 604/74 |
| 4,740,202 | 4/1988 | Stacey et al. ........................ 604/119 |
| 4,772,262 | 9/1988 | Grant et al. ............................ 604/74 |
| 4,813,931 | 3/1989 | Hauze ..................................... 604/54 |
| 4,857,051 | 8/1989 | Larsson .................................. 604/74 |
| 4,886,494 | 12/1989 | Morifuji ................................. 604/74 |
| 4,892,517 | 1/1990 | Yuan et al. ............................. 604/74 |
| 4,911,405 | 3/1990 | Weissgerber ..................... 251/129.14 |
| 4,915,691 | 4/1990 | Jones et al. ............................ 604/74 |
| 4,929,229 | 5/1990 | Larsson .................................. 604/74 |
| 4,961,726 | 10/1990 | Richter ................................... 604/74 |
| 4,964,851 | 10/1990 | Larsson .................................. 604/74 |
| 5,007,899 | 4/1991 | Larsson .................................. 604/74 |
| 5,071,403 | 12/1991 | Larsson .................................. 604/74 |
| 5,098,414 | 3/1992 | Walker ................................. 604/291 |
| 5,100,406 | 3/1992 | Panchula ................................ 604/74 |
| 5,295,957 | 3/1994 | Aida et al. ............................. 604/74 |
| 5,358,476 | 10/1994 | Wilson ................................... 604/74 |
| 5,542,921 | 8/1996 | Meyer et al ........................... 604/74 |
| 5,571,084 | 11/1996 | Palmer ................................... 604/74 |
| 5,601,531 | 2/1997 | Silver .................................... 604/74 |
| 5,720,722 | 2/1998 | Lockridge ............................. 604/74 |
| 5,776,098 | 7/1998 | Silver et al. ........................... 604/74 |
| 5,810,772 | 9/1998 | Niederberger ......................... 604/74 |

Primary Examiner—Wynn Wood Coggins
Assistant Examiner—Michael M. Thompson
Attorney, Agent, or Firm—Thomas Hine & Flory LLP

[57] ABSTRACT

A self cycling breast pump including a nurser bottle and a suction assembly adapted to be situated on a breast of a human for delivering milk to the nurser bottle upon the application of a suction thereto. Further provided is an electric pump adapted to generate a vacuum at an inlet upon the activation thereof. The inlet of the electric pump is connected to the suction assembly. Also included is an electronic vent valve adapted to vent the vacuum created by the electric pump upon the activation thereof for releasing the vacuum. Associated therewith is vent control circuitry for determining a rate of activation of the electric vent valve thereby creating a cycling suction at the inlet of the electric pump. Vacuum control circuitry is provided for allowing the manual governing of the level of vacuum generated by the electric pump means. This is accomplished by controlling the speed of a motor associated with the pump.

18 Claims, 4 Drawing Sheets

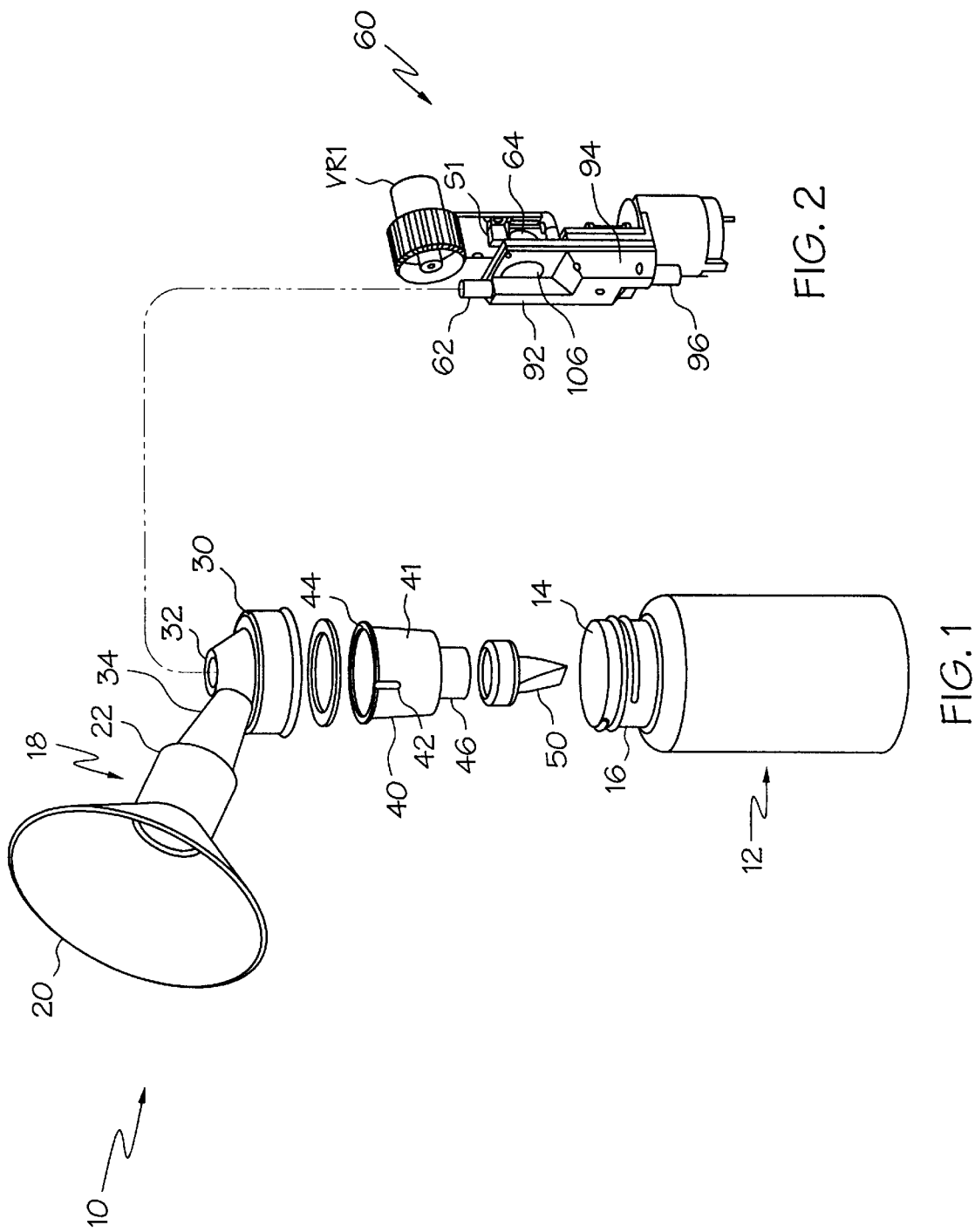

SELF-CYCLING BREAST PUMP

BACKGROUND OF THE INVENTION

1. Field of the Invention

The present invention relates to a self cycling breast pump and more particularly pertains to automatically venting a vacuum afforded by a breast pump at a predetermined rate.

2. Description of the Prior Art

The use of breast pumps is known in the prior art. More specifically, breast pumps heretofore devised and utilized for the purpose of extracting milk from a human breast are known to consist basically of familiar, expected and obvious structural configurations, notwithstanding the myriad of designs encompassed by the crowded prior art which have been developed for the fulfillment of countless objectives and requirements.

By way of example, the prior art includes U.S. Pat. No. 3,782,385 to Loyd; U.S. Pat. No. 4,323,067 to Adams; U.S. Pat. No. 4,263,912 to Adams; U.S. Pat. No. 4,573,969 to Schlensog et al; U.S. Pat. No. 3,824,709 to Knapp et al.; U.S. Pat. No. 4,583,970 to Kirchner; U.S. Pat. No. 4,740,196 to Powell; U.S. Pat. No. 4,772,262 to Grant et al.; U.S. Pat. No. 4,586,612 to Dahan; U.S. Pat. No. 4,759,747 to Aida et al; U.S. Pat. No. 5,295,957 to Aida et al.; U.S. Pat. No. 5,071,403 to Larsson; U.S. Pat. No. 4,964,851 to Larsson; U.S. Pat. No. 4,961,726 to Richter; U.S. Pat. No. 4,929,229 to Larsson; U.S. Pat. No. 4,911,405 to Weissgerber; U.S. Pat. No. 5,542,921 to Meyers et al; U.S. Pat. No. 4,673,388 to Schlensog et al.; and U.S. Pat. No. 1,847,658 to Lasker.

In this respect, the self cycling breast pump according to the present invention substantially departs from the conventional concepts and designs of the prior art, and in so doing provides an apparatus primarily developed for the purpose of automatically venting a vacuum applied by a breast pump at a predetermined rate.

Therefore, it can be appreciated that there exists a continuing need for a new and improved self cycling breast pump which can be used for automatically venting a vacuum applied by a breast pump at a predetermined rate. In this regard, the present invention substantially fulfills this need.

SUMMARY OF THE INVENTION

In view of the foregoing disadvantages inherent in the known types of breast pumps now present in the prior art, the present invention provides an improved self cycling breast pump. As such, the general purpose of the present invention, which will be described subsequently in greater detail, is to provide a new and improved self cycling breast pump which has all the advantages of the prior art and none of the disadvantages.

To attain this, the present invention essentially comprises a nurser bottle with a circular opening formed on a top face thereof. As shown in FIG. 1, the nurser bottle has a peripheral lip integrally formed about the top opening with a plurality of coaxial threads formed thereon. Further provided is a suction assembly having an outboard extent with a frusto-conical configuration. The outboard extent has a large opening and a small opening. The suction assembly further includes an inboard extent having a cylindrical configuration integrally formed in coaxial relation with the small opening of the outboard extent. With reference still to FIG. 1, a cap assembly is included with a top face and a periphery integrally formed thereto and depending downwardly therefrom. The periphery has a plurality of threaded grooves formed in an inner surface thereof. The top face of the cap assembly has an aperture formed in a central extent thereof. For allowing connection of the suction assembly thereto, the cap assembly further includes a mounting tube integrally coupled at first end thereof to the top face of the cap assembly and in communication with an interior thereof. By this structure, the inboard extent of the suction assembly may be frictionally engaged with the mounting tube. A reservoir is included with an upper extent formed of a bottom face with an aperture formed therein. A cylindrical periphery is integrally formed with the bottom face and extended upwardly therefrom to define a top opening. For reasons that will become apparent later, a plurality of grooves are formed in the periphery adjacent the top opening of the reservoir. An annular flange is formed along the periphery of the reservoir contiguous with the top opening thereof for resting about the peripheral lip of the nurser bottle such that the cap assembly may be threadedly secured to the nurser bottle. The reservoir further includes a lower extent formed of a vertically oriented tube integrally coupled to the bottom face of the upper extent about the aperture thereof. Coupled to the lower extent of the reservoir is a one-way valve for allowing liquid received from the suction assembly to pass therethrough to the nurser bottle. As generally, shown in FIG. 2, electric pump means is included for generating a vacuum at an inlet thereof upon the activation thereof. Associated therewith is electronic vacuum control means adapted for allowing the manual governing of the level of vacuum generated by the electric pump means. Further provided is electric vent valve means adapted to vent the vacuum created by the electric pump means upon the activation thereof for releasing said vacuum. As can be seen in FIGS. 3 & 4, the electric pump means and vent valve means comprise an upper housing with a planar top face and a planar bottom face. The upper housing has a circular inset portion with a plurality of apertures situated in a first half thereof. Such apertures extend between a bottom of the circular inset portion and the bottom face of the upper housing. Associated therewith is a semicircular cut out formed in a second half of the circular inset portion. The semicircular cut out also extends between the top face and the bottom face of the upper housing. Further provided is an atmospheric vent formed of a square aperture extending between the top face and the bottom face of the upper housing. A pair of vent apertures are formed through the upper housing and are connected via a vent crossover tube situated on the top face of the upper housing. As best shown in FIG. 3, a vent valve passage is defined by a groove formed in the bottom face of the upper housing which is in communication with one of the vent apertures and extends to a point adjacent the atmospheric vent. The electric pump means and the vent valve means further includes a lower housing positioned beneath the upper housing. The lower housing has a bottom face and a planar top face. A first compartment is situated on the bottom face in communication with the inlet of the pump means. A second compartment is situated on the bottom face in communication with an exhaust port. Formed in the top face in communication with the second compartment is a semicircular cut out. Such semicircular cut out is situated directly beneath the plurality of apertures which are positioned in the circular inset portion of the upper housing. Associated therewith is a plurality of apertures formed in the top face of the lower housing and in communication with the first compartment. The plurality of apertures of the lower housing are situated directly beneath the semicircular cut out situated in the circular inset portion of the upper housing. A vent aperture is formed in the top face of the lower housing. Such vent aperture is designed to remain in communication with the first compartment of the lower housing and the vent aperture, of the upper housing which is not in communication with the groove. A circular cut out is formed in the lower housing and extended between the top face and the bottom face thereof. Still yet another component of the electric pump means and the vent valve means is a planar elastomeric sheet. Such sheet is situated between the upper housing and the lower housing. Formed in the sheet of elastomeric material is a plurality of flaps situated over the apertures of the lower housing and the apertures located in the circular inset portion of the upper housing. It should be noted that the elastomeric sheet further resides between the circular cut out of the lower housing and the pair of apertures and atmospheric vent of the upper housing. The elastomeric sheet has an aperture formed therein for allowing communication between the vent aperture of the lower housing and the associated vent aperture of the upper housing. As shown in FIG. 4, the electric pump means further includes a diaphragm sealed about the circular inset portion of the upper housing. The diaphragm has a tab centrally coupled to a top face thereof with a bore formed therein. The electric pump means further has a motor with an eccentrically configured post coupled to a rotor thereof. As such, the post may be rotatably situated within the bore of the tab and upon the actuation of the motor, the tab and the diaphragm are moved up and down. This effects the suction of air through the apertures of the lower housing and expelling of air through the apertures of the upper housing thus creating a vacuum at the inlet of the electric pump means. With reference still to FIG. 4, the vent valve means also includes a plunger with a cylindrical configuration slidably situated within the atmospheric vent for biasing the elastomeric sheet within the circular cut out of the lower housing upon the actuation thereof. Upon such biasing, a vacuum residing in the first compartment is released through the atmospheric vent via the vent crossover tube and groove.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved self cycling breast pump which has all the advantages of the prior art breast pumps and none of the disadvantages.

It is another object of the present invention to provide a new and improved self cycling breast pump which may be easily and efficiently manufactured and marketed.

It is a further object of the present invention to provide a new and improved self cycling breast pump which is of a durable and reliable construction.

An even further object of the present invention is to provide a new and improved self cycling breast pump which is susceptible of a low cost of manufacture with regard to both materials and labor, and which accordingly is then susceptible of low prices of sale to the consuming public, thereby making such self cycling breast pump economically available to the buying public.

Still yet another object of the present invention is to provide a new and improved self cycling breast pump which provides in the apparatuses and methods of the prior art some of the advantages thereof, while simultaneously overcoming some of the disadvantages normally associated therewith.

Still another object of the present invention is to automatically vent a vacuum applied by a breast pump at a predetermined rate.

Yet another object of the present invention is to allow manual adjustment of a level of suction afforded by the pump by means of controlling the speed of the motor which operates the pump.

Another object of the present invention is to provide an self cycling means which operates independently with respect to slight variations in power supplied thereto.

Still yet another object of the present invention is provide a breast pump that operates in a more efficient manner.

Lastly, it is an object of the present invention to provide a new and improved self cycling breast pump including a nurser bottle and a suction assembly adapted to be situated on a breast of a human for delivering milk to the nurser bottle upon the application of a suction thereto. Further provided is an electric pump adapted to generate a vacuum at an inlet thereof upon the activation thereof. The inlet of the electric pump is connected to the suction assembly. Also included is an electronic vent valve adapted to vent the vacuum created by the electric pump upon the activation thereof for releasing the vacuum. Associated therewith is vent control circuitry for determining a rate of activation of the electric vent valve thereby creating a cycling suction at the inlet of the electric pump. Vacuum control circuitry is provided for allowing the manual governing of the level of vacuum generated by the electric pump means. This is accomplished by controlling the speed of a motor associated with the pump.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective illustration of the preferred embodiment of the self cycling breast pump constructed in accordance with the principles of the present invention.

FIG. 2 is a perspective illustration of the electric pump means and electric vent valve means of the present invention.

Similar reference characters refer to similar parts throughout the several views of the drawings.

DESCRIPTION OF THE PREFERRED EMBODIMENT

Figure 3:
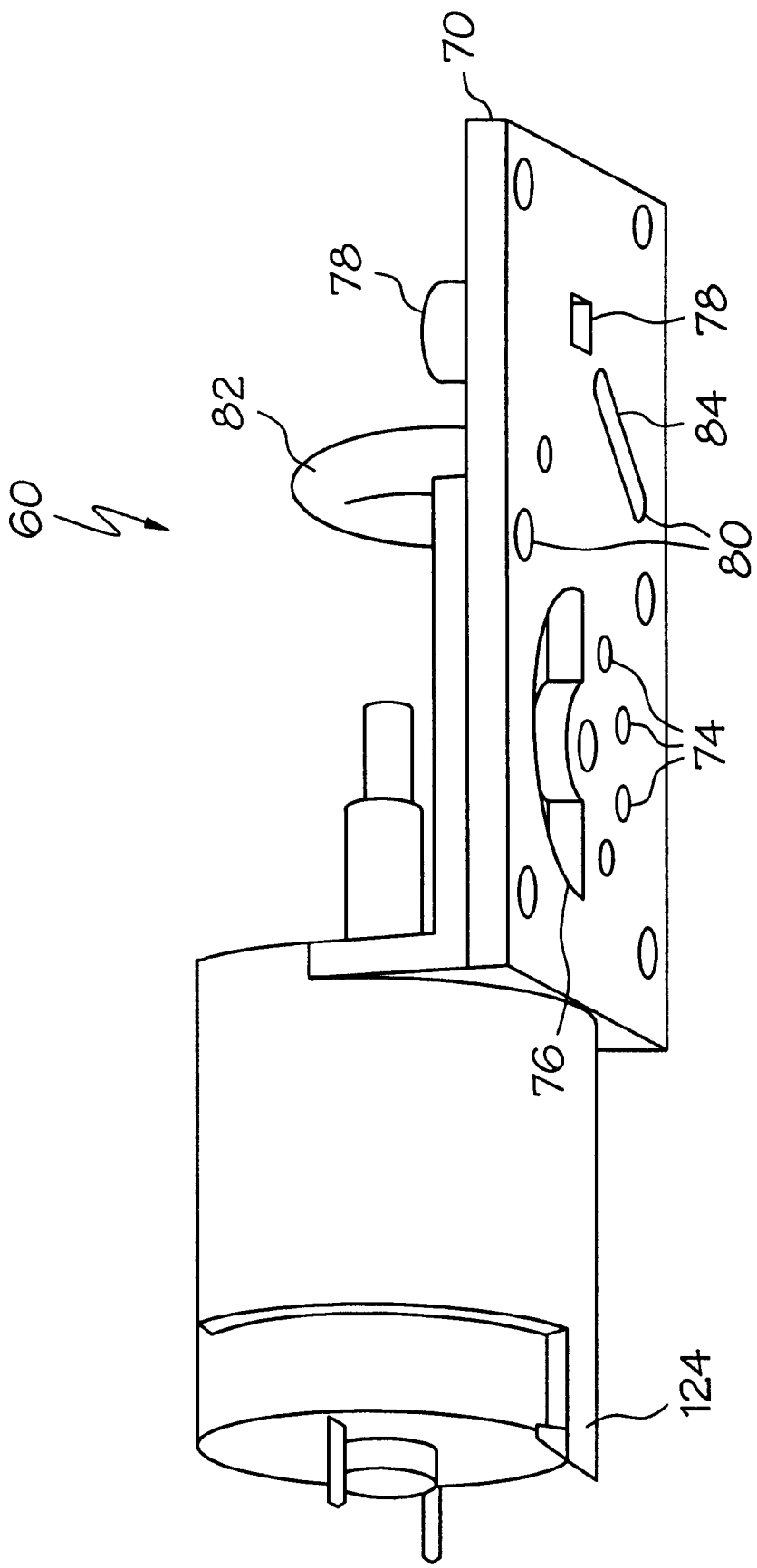
FIG. 3 is a side elevational view of the upper housing and motor of the electric pump means of the present invention.

With reference now to the drawings, and in particular to FIG. 1 thereof, a new and improved self cycling breast pump embodying the principles and concepts of the present invention and generally designated by the reference numeral 10 will be described.

The present invention, the new and improved self cycling breast pump, is comprised of a plurality of components. Such components in their broadest context include a nurser bottle, suction assembly, cap assembly, reservoir, one-way valve, electric pump means, electronic vacuum control means, electric valve vent means, electronic valve vent control means, and low battery indicator means. Such components are individually configured and correlated with respect to each other so as to attain the desired objective.

More specifically, it will be noted that the system 10 of the present invention includes a nurser bottle 12 with a circular opening 14 formed on a top face thereof. As shown in FIG. 1, the nurser bottle 12 has a peripheral lip 16 integrally formed about the top opening with a plurality of coaxial threads formed thereon.

Further provided is a suction assembly 18 having an outboard extent 20 with a frusto-conical configuration. The outboard extent 20 has a large opening and a small opening. The suction assembly 18 further includes an inboard extent 22 having a cylindrical configuration integrally formed in coaxial relation with the small opening of the outboard extent 20.

With reference still to FIG. 1, a cap assembly 30 is included with a top face and a periphery integrally formed thereto and extending downwardly therefrom. The periphery has at least one groove formed in an inner surface thereof. The top face of the cap assembly 30 has an aperture 32 formed in a central extent thereof. For allowing connection of the suction assembly 18 thereto, the cap assembly 30 further includes a mounting tube 34 integrally coupled at first end thereof to the top face of the cap assembly 30 and in communication with an interior thereof. By this structure, the inboard extent of the suction assembly 18 may be frictionally engaged with the mounting tube 34 at predetermined angle of approximately 45 degrees.

A reservoir 40 is included with an upper extent 41 formed of a bottom face with an aperture formed therein. A cylindrical periphery is integrally formed with the bottom face and extended upwardly therefrom to define a top opening. For reasons that will become apparent later, a plurality of grooves 42 are formed in an exterior surface of the periphery adjacent the top opening of the reservoir 40. An annular flange 44 is formed along the periphery of the reservoir 40 contiguous with the top opening thereof for resting about the peripheral lip 16 of the nurser bottle 12 such that the cap assembly may be threadedly secured to the nurser bottle 12 with an unnumbered gasket situated therebetween. Note that the grooves 42 also extend along a lower surface of the flange 44. When the cap assembly 30 is secured on the nurser bottle, it is imperative that the grooves 42 provide a passage between the interior space of the nurser bottle and the atmosphere. The reservoir 40 further includes a lower extent 46 formed of a vertically oriented tube integrally coupled to the bottom face of the upper extent about the aperture thereof.

Coupled to the lower extent of the reservoir 40 is a one-way valve 50 for allowing liquid received from the suction assembly 18 to pass therethrough to the nurser bottle 12.

By this structure, a suction may be applied at the aperture of the cap assembly 30 such that the interior space thereof and the area within the reservoir 40 may be evacuated. Evacuation of the nurser bottle is prevented by the one-way valve 50. The evacuation of the cap assembly 30 and reservoir 40 effects removal of milk from a breast inserted within the suction assembly 18. When the milk flows to the reservoir 40, it flows through the one-way valve 50 by means of gravity. Equalization of air within the nurser bottle as it is filled with milk is accomplished via the grooves 42.

As generally shown in FIG. 2, electric pump means 60 is included for affording the above mentioned vacuum. The electric pump means generates the vacuum at an inlet 62 thereof upon the activation thereof. It should be noted that an unillustrated suction tube is connected between the inlet 62 of the electric pump means and the aperture formed on the cap assembly 30.

Further provided is electric vent valve means 64 (see FIG. 4) adapted to vent the vacuum created by the electric pump means upon the activation thereof for releasing the vacuum.

Figure 4:
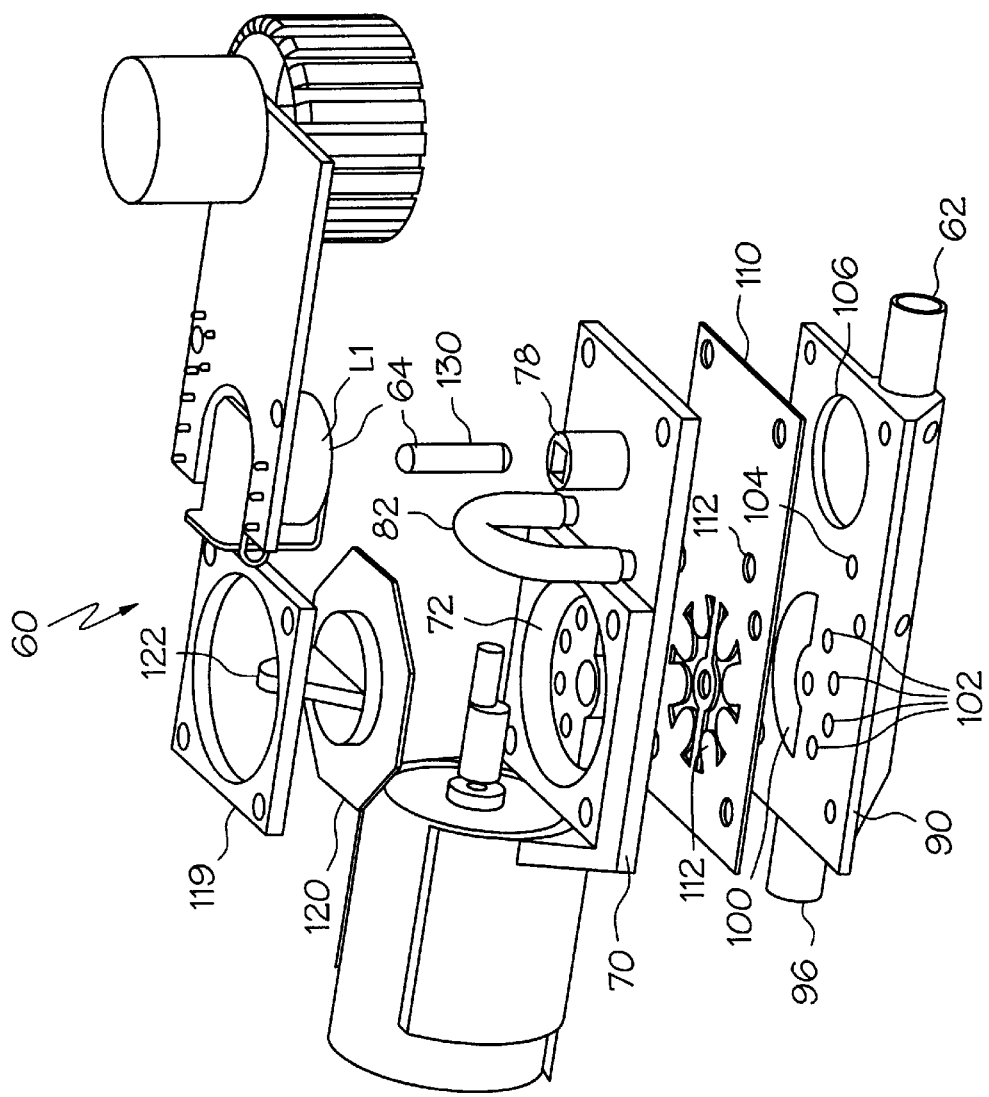
FIG. 4 is an exploded view of the present invention depicting the upper housing, lower housing, elastomeric sheet, and various other components thereof.

As can be seen in FIGS. 3 & 4, the electric pump means and vent valve means comprise an upper housing 70 with a planar top face and a planar bottom face. The upper housing 70 has a circular inset portion 72 with a plurality of apertures 74 situated in a first half thereof. Such apertures extend between a bottom of the circular inset portion and the bottom face of the upper housing 70. Associated therewith is a semicircular cut out 76 formed in a second half of the circular inset portion 72. The semicircular cut out 76 also extends between the top face and the bottom face of the upper housing 70. Further provided is an atmospheric vent 78 formed of a square aperture extending between the top face and the bottom face of the upper housing 70. A pair of vent apertures 80 are formed through the upper housing 70 and are connected via a vent crossover tube 82 situated on the top face of the upper housing 70. As best shown in FIG. 3, a vent valve passage is defined by a groove 84 formed in the bottom face of the upper housing 70 which is in communication with one of the vent apertures 80 and extends to a point adjacent the atmospheric vent 78.

The electric pump means and the vent valve means further includes a lower housing 90 positioned beneath the upper housing 70. The lower housing 90 has a bottom face and a planar top face. A first compartment 92 is situated on the bottom face in communication with the inlet 62 of the pump means. A second compartment 94 is situated on the bottom face in communication with an exhaust port 96. Formed in the top face of the lower housing and in communication with the second compartment 94 is a semicircular cut out 100.

Such semicircular cut out 100 is situated directly beneath the plurality of apertures 74 which are positioned in the circular inset portion 72 of the upper housing 70. Associated therewith is a plurality of apertures 102 formed in the top face of the lower housing 90 and in communication with the first compartment 92. The plurality of apertures 102 of the lower housing 90 are situated directly beneath the semicircular cutout 76 situated in the circular inset portion 72 of the upper housing 70. A vent aperture 104 is formed in the top face of the lower housing 90. Such vent aperture 104 is designed to remain in communication with the first compartment 92 of the lower housing 90 and the vent aperture, of the upper housing 70 which is not in communication with the groove. A circular cut out 106 is formed in the lower housing 90 and is further extended between the top face and the bottom face thereof.

Still yet another component of the electric pump means and the vent valve means is a planar elastomeric sheet 110. Such sheet is situated between the upper housing 70 and the lower housing 90. Formed in the sheet of elastomeric material is a plurality of flaps 112 situated over the apertures 102 of the lower housing 90 and the apertures 74 located in the circular inset portion 72 of the upper housing 70. It should be noted that the elastomeric sheet 110 further resides between the circular cut out 106 of the lower housing 90 and the pair of apertures and atmospheric vent 78 of the upper housing 70. The elastomeric sheet 110 has an aperture 112 formed therein for allowing continuous communication between the vent aperture 104 of the lower housing 90 and the associated vent aperture of the upper housing 70.

As shown in FIG. 4, the electric pump means further includes a diaphragm 120 sealed about the circular inset portion 72 of the upper housing 70 by means of a retainer 119. The diaphragm 120 has a tab 122 centrally coupled to a top face thereof with a bore formed therein. The electric pump means further has a motor 124 with an eccentrically configured post coupled to a rotor thereof. As such, the post may be rotatably situated within the bore of the tab 122 and upon the actuation of the motor 124, the tab 122 and the diaphragm 120 are moved up and down. This effects the suction of air through the apertures 102 of the lower housing 90 and expelling of air through the apertures 74 of the upper housing 70 thus creating a vacuum at the inlet 62 of the electric pump means while expelling air out the exhaust port 96. The flaps of the elastomeric sheet ensure one-way passage of air through the respective apertures. Passage of air is afforded by allowing the flaps to move within the associated semicircular cut out away from their respective apertures. The exhaust port is ideally situated exterior a housing in which the above components reside. As such, when the system is flushed with water, it may be expelled without contacting any of the vital components positioned in the housing.

With reference still to FIG. 4, the vent valve means 64 also includes a plunger 130 with a cylindrical configuration slidably situated within the atmospheric vent 78 for biasing the elastomeric sheet 110 within the circular cut out 106 of the lower housing 90 upon the actuation thereof. This allows communication between the atmospheric vent 78 and the groove 84. Upon such communication, a vacuum residing in the first compartment 92 is released through the atmospheric vent 78 via the vent crossover tube 82 and groove 84.

Figure 5:
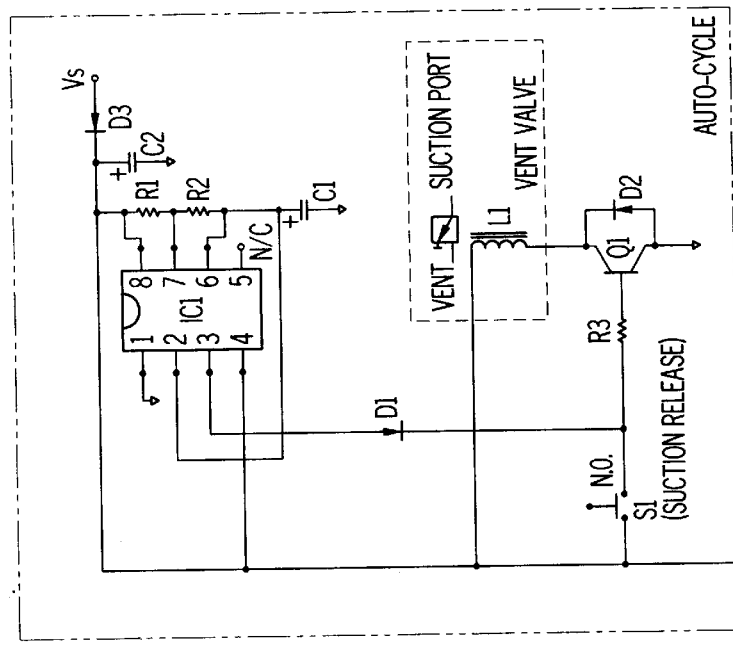
FIG. 5 is a schematic diagram of the vent valve control means and the low battery indicator means of the present invention.

For affording intermittent suction at the inlet 62 of the electric pump means, electronic vent control means 140 is provided. The electronic vent control means 140 is adapted for determining a rate of activation of the electric vent valve means thereby creating an automatic cycling suction at the inlet 62 of the electric pump means. As shown in FIG. 5, the electronic vent control means 140 preferably comprises a 555 timer IC1 designed for astable operation. The 555 is adapted to produce a square wave at an output thereof upon the receipt of power. Such square wave has a duty cycle which is determined by the selection of resistor R1, resistor R2, and capacitor C1, as is commonly known in the art. As will become apparent hereinafter, the duty cycle is preferably tailored to effect a suction/release cycle which resembles that of a child. Such suction/release cycle consists of an approximate 1 second suction and a 1 second release. As shown in FIG. 5, the output of the 555 timer is connected to a diode D1 which is in turn connected to a base of a transistor Q1. The transistor Q1 is connected at its collector to a solenoid in which the plunger of the electronic vent control means is situated to define a transducer. The transistor Q1 operates as an amplified switch in that upon the receipt of a high pulse, the solenoid is actuated with a sufficient current thereby forcing the plunger against the elastomeric sheet 110. This, in turn, vents the vacuum of the first compartment 92. It should be noted that a diode D2 is coupled between the collector and the emitter of the transistor to preclude a reverse polarity voltage across transistor Q1 during deactivation. As an option, the transistor may be removed in favor of a substitute for the 555 timer IC1 which is capable of producing sufficient current for the proper operation of the traducer and solenoid combination. Still yet another option is to utilize a coil L1 with a higher DC resistance in lieu of the transistor Q1. Both alternatives are feasible and should be designed with the amount of necessary force afforded by the plunger in mind.

To manually release the vacuum at the inlet 62 of the electric pump means, a manual vent control means may be utilized. Preferably, such manual vent control means includes a switch S1 connected between a source of power and the base of the transistor Q1. By this structure, an artificial high pulse is generated upon the depression of such switch. The function of diode D1 now becomes apparent in that it functions to prevent a short circuit through pin 3 of 555 timer IC1 when pin 3 of the 555 timer IC1 is low.

Figure 6:
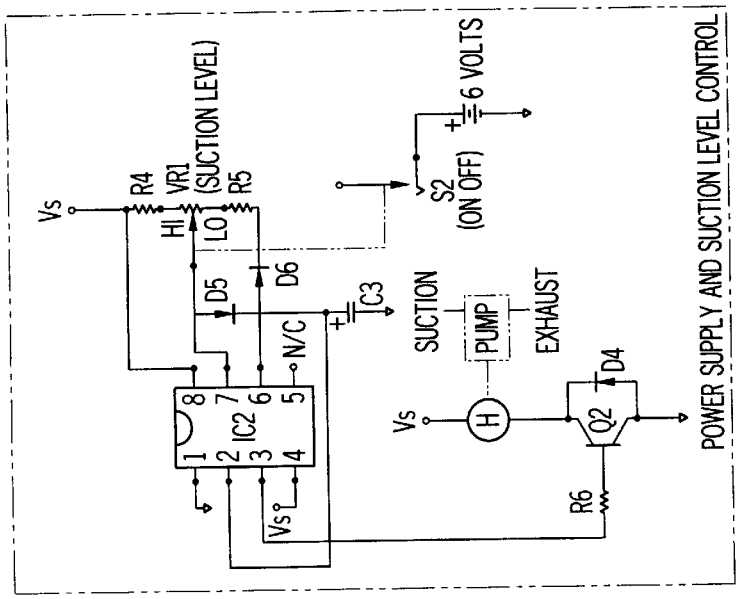
FIG. 6 is a schematic diagram of the electronic vacuum control means.

With reference now to FIG. 6, it is shown that an electronic vacuum control means 150 is provided. Such electronic vacuum control means 150 is adapted for allowing the manual governing of the level of vacuum generated by the electric pump means. To accomplish such, the speed of the motor 124 of the electric pump means is governed. The speed of the motor 124 is controlled by means of a variable duty oscillator IC2. The component type of IC2 is the same as IC1. A plurality of resistors R4 & R5, diodes D5 & D6, and a capacitor C3 are configured to dictate the specific operation of IC2. Also included is a potentiometer VR1 which has an associated dial 152 available for manipulation by a user. The potentiometer VR1 allows a user to govern the duty cycle of the pulse which is transmitted from the output of the variable duty oscillator IC2. The output of the variable duty oscillator IC2 is in turn connected to the base of a transistor Q2. Such transistor Q2 is connected at a collector thereof to the motor 124. In use, the speed of the motor 124 and the suction thereby afforded is increased and decreased upon the variation of the duty cycle via the dial. It should be noted that the average voltage or DC voltage at the output of the IC2 is proportional to the duty cycle and further the voltage delivered to the motor 124 is the amplitude of the output pulse of the oscillator IC2 minus the voltage drop across the transistor Q2. A diode D4 is connected between the collector and emitter of the transistor for reasons similar to that of transistor Q1. The frequency of the pulse at the output of IC2 has no effect on the speed of the motor 124 and therefore is deemed not critical except that lower frequencies(30 Hz) result in higher available motor torque especially at lower motor speeds. It should be noted that the potentiometer is of the type equipped with a switch S2 that is open when the dial 152 is turned entirely in a clockwise direction. A detent is formed on the shaft of the potentiometer VR1 to indicate whether the dial is turned entirely in the clockwise direction. Such switch S2 allows a user to selectively supply power to the electronic components of the present invention.

For monitoring a portable power supply such as a battery, a low battery indication means 160 is provided for alerting a user upon an available power of the battery falling below a predetermined level. While the present invention is ideally equipped to accommodate power supplied by a battery, it should be noted that the present invention may also be powered by a conventional power receptacle. While not illustrated, the present invention includes an AC adapter with an associated switch which disconnects the batteries from the associated circuitry upon the employment of the AC adapter. As shown in FIG. 5, the low battery indication means includes a chip IC3 which is identical to IC1 & IC2 utilized in the previous circuits. In use, when the batteries discharge to a voltage of approximately 4 Volts, a light emitting diode D7 actuates such that it is visible to a user. The ratio of a pair of associated resistors R7 & R8 along with the zener diode D8 determine the threshold voltage at which the light emitting diode is actuated. The present invention is equipped with numerous features for affording high efficiency. The apertures 74 & 102 of the upper and lower housing 90 are 0.095 in diameter and the inlet 62 and exhaust port 96 of the electric pump means are no less than 0.20 inches, inside diameter. This is to minimize pressure loss as air passes therethrough. Further, by the utilization of the reservoir 40, the amount of the volume required to be evacuated is reduced thus lessening the amount of power required.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A new and improved self cycling breast pump comprising, in combination:
   a nurser bottle with a circular opening formed on a top face thereof, the nurser bottle having a peripheral lip integrally formed about the top opening with a plurality of coaxial threads formed thereon;
   a suction assembly having an outboard extent with a frusto-conical configuration, the outboard extent having a large opening and a small opening, the suction assembly further having an inboard extent having a cylindrical configuration integrally formed in coaxial relation with the small opening of the outboard extent;
   a cap assembly including a top face and a periphery integrally formed thereto and depending downwardly therefrom with a plurality of threaded grooves formed in an inner surface thereof, the top face having an aperture formed in a central extent thereof, the cap assembly further including a mounting tube integrally coupled at first end thereof to the top face of the cap assembly and in communication with an interior thereof, the mounting tube adapted to allow frictional coupling of the inboard extent of the suction assembly thereto;
   a reservoir including an upper extent formed of a bottom face with an aperture formed therein, a cylindrical periphery integrally formed with the bottom face and extending upwardly to define a top opening, a plurality of grooves formed in the periphery adjacent the top opening of the reservoir, and an annular flange formed along the periphery of the reservoir contiguous with the top opening thereof for resting about the peripheral lip of the nurser bottle such that the cap assembly may be threadedly secured to the nurser bottle, the reservoir further including a lower extent formed of a vertically oriented tube integrally coupled to the bottom face of the upper extent about the aperture thereof;
   a one-way valve adapted to be frictionally coupled to the lower extent of the reservoir for allowing liquid received from the suction assembly to pass therethrough to the nurser bottle;
   electric pump means adapted to generate a vacuum at an inlet thereof upon the activation thereof;
   electronic vacuum control means for allowing the manual governing of the level of vacuum generated by the electric pump means;
   electric vent valve means adapted to vent the vacuum created by the electric pump means upon the activation thereof for releasing said vacuum;
   manual vent control means adapted to vent the vacuum created by the electric pump means upon the manual activation thereof for releasing said vacuum;
   electronic vent control means for determining a rate of activation of the electric vent valve means thereby creating a cycling suction at the inlet of the electric pump means; and
   low battery indication means coupled to a battery for alerting a user upon an available power of the battery falling below a predetermined level.

2. A self cycling breast pump comprising:
   a nurser bottle;
   a suction assembly adapted to be situated on a breast of a human for delivering milk to the nurser bottle upon the application of a suction thereto;
   electric pump means adapted to generate a vacuum at an inlet thereof upon the activation thereof, wherein the inlet is connected to the suction assembly;
   electric vent valve means adapted to vent the vacuum created by the electric pump means upon the activation thereof for releasing said vacuum; and
   electronic vent control means for determining a rate of activation of the electric vent valve means thereby creating a predetermined cycling suction at the inlet of the electric pump means.

3. A self cycling breast pump as set forth in claim 2 wherein the electric vent valve means includes a solenoid and a plunger.

4. A self cycling breast pump as set forth in claim 2 and further including low battery indication means coupled to a battery for alerting a user when an available power of the battery falls below a predetermined level.

5. A self cycling breast pump as set forth in claim 2 wherein the electronic vent control means includes a 555 timer.

6. An self cycling breast pump as set forth in claim 2 wherein the electronic vent control means vents the vacuum created by the electric pump means at a constant rate independent of slight variations in power supplied thereto.

7. A self cycling breast pump as set forth in claim 2 wherein the electric pump means and vent valve means comprise an upper housing with a planar top face and a planar bottom face, the upper housing having a circular inset portion with a plurality of apertures situated on a first half thereof which extend between the top face and the bottom face thereof and a semicircular cut out formed in a second half thereof which also extends between the top face and the bottom face thereof, an atmospheric vent formed of a square aperture extending between the top face and the bottom face of the upper housing, a pair of vent apertures connected via a vent crossover tube situated on the top face of the upper housing, and a vent valve passage including a groove formed in the bottom face of the upper housing which is in communication with one of the vent apertures and extends to a point adjacent the atmospheric vent; the electric pump means and the vent valve means further including a lower housing positioned beneath the upper housing and having a bottom face and a planar top face, a first compartment situated on the bottom face in communication with the inlet of the pump means, a second compartment situated on the bottom face in communication with an exhaust port, a semicircular cut out formed in the top face and in communication with the second compartment wherein the semicircular cut out of the lower housing is situated directly beneath the plurality of apertures situated in the circular inset portion of the upper housing, a plurality of apertures formed in the top face of the lower housing and in communication with the first compartment wherein the plurality of apertures of the lower housing re situated directly beneath the semicircular cut out situated in the circular inset portion of the upper housing, a vent aperture formed in the top face of the lower housing in communication with the first compartment of the lower housing and the vent aperture of the upper housing which is not in communication with the groove, and a circular cut out formed in the lower housing and extending between the top face and the bottom face thereof; the electric pump means and the vent valve means further including a planar elastomeric sheet situated between the upper housing and the lower housing including a plurality of flaps formed therein with the flaps situated over the apertures of the lower housing and the apertures located in the circular inset portion of the upper housing, the elastomeric sheet further situated between the circular cut out of the lower housing and the pair of apertures and atmospheric vent of the upper housing, wherein the elastomeric sheet has an aperture formed therein for allowing communication between the vent aperture of the lower housing and the associated vent aperture of the upper housing.

8. A self cycling breast pump as set forth in claim 7 wherein the electric pump means includes a diaphragm sealed about the circular inset portion of the upper housing, the diaphragm having a tab centrally coupled to a top face thereof with a bore formed therein, the electric pump means further including a motor with an eccentrically configured post coupled to a rotor thereof wherein the post may be rotatably situated within the bore of the tab, whereby upon the actuation of the motor, the tab and the diaphragm are moved up and down thereby allowing the suction of air through the apertures of the lower housing and expelling of air through the apertures of the upper housing thus creating a vacuum at the inlet of the electric pump means.

9. A self cycling breast pump as set forth in claim 8 wherein the vent valve means includes a plunger with a cylindrical configuration slidably situated within the atmospheric vent for biasing the elastomeric sheet within the circular cut out of the lower housing upon the actuation thereof, whereby upon said biasing, a vacuum residing in the first compartment is released through the atmospheric vent via the vent crossover tube and groove.

10. A self cycling breast pump as set forth in claim 2 and further including manual vent control means adapted to vent the vacuum created by the electric pump means upon the manual activation thereof for releasing said vacuum.

11. A self cycling breast pump as set forth in claim 10 wherein the manual vent valve means includes a switch which is adapted to effect releasing of said vacuum.

12. A self cycling breast pump as set forth in claim 2 wherein the nurser bottle includes a circular opening formed on a top face thereof, the nurser bottle having a peripheral lip integrally formed about the top opening with a plurality of coaxial threads formed thereon.

13. A self cycling breast pump as set forth in claim 12 wherein the suction assembly includes an outboard extent with a frusto-conical configuration, the outboard extent having a large opening and a small opening, the suction assembly further having an inboard extent having a cylindrical configuration integrally formed in coaxial relation with the small opening of the outboard extent.

14. A self cycling breast pump as set forth in claim 13 and further including a cap assembly including a top face and a periphery integrally formed thereto and depending downwardly therefrom with a plurality of threaded grooves formed in an inner surface thereof, the top face having an aperture formed in a central extent thereof, the cap assembly further including a mounting tube integrally coupled at first end thereof to the top face of the cap assembly and in communication with an interior thereof, the mounting tube adapted to allow frictional coupling of the inboard extent of the suction assembly thereto.

15. A self cycling breast pump as set forth in claim 14 and further including a reservoir having an upper extent formed of a bottom face with an aperture formed therein, a cylindrical periphery integrally formed with the bottom face and extending upwardly to define a top opening, a plurality of grooves formed in the periphery adjacent the top opening of the reservoir, and an annular flange formed along the periphery of the reservoir contiguous with the top opening thereof for resting about the peripheral lip of the nurser bottle such that the cap assembly may be threadedly secured to the nurser bottle, the reservoir further including a lower extent formed of a vertically oriented tube integrally coupled to the bottom face of the upper extent about the aperture thereof.

16. A self cycling breast pump as set forth in claim 15 and further including a one-way valve adapted to be frictionally coupled to the lower extent of the reservoir for allowing liquid received from the suction assembly to pass therethrough to the nurser bottle.

17. A self cycling breast pump comprising:

a nurser bottle;

a suction assembly adapted to be situated on a breast of a human for delivering milk to the nurser bottle upon the application of a suction thereto;

electric pump means adapted to generate a vacuum at an inlet thereof upon the activation thereof, wherein the inlet is connected to the suction assembly; and electronic vacuum control means for allowing the manual governing of the level of vacuum generated by the electric pump means;

wherein the electric pump means comprises a motor which operates at a speed governed by the electronic vacuum control means; and electric vent valve means adapted to vent the vacuum created by the electric pump means upon the activation thereof for releasing said vacuum.

18. A self cycling breast pump as set forth in claim 17 wherein the electronic vacuum control means includes a variable duty cycle oscillator.

* * * * *